US012676216B2

(12) United States Patent
Beeler et al.

(10) Patent No.: US 12,676,216 B2
(45) Date of Patent: Jul. 7, 2026

(54) SYSTEMS AND METHODS FOR UTILIZING DATA OBJECT REFERENCES TO MERGE A PROGRAM

(71) Applicant: ICON CLINICAL RESEARCH LIMITED, Leopardstown (IE)

(72) Inventors: Jeff Beeler, Cary, NC (US); Matt Sabol, Springfield, VA (US); John Bigley, Lincoln, CA (US)

(73) Assignee: ICON CLINICAL RESEARCH LIMITED

( * ) Notice: Subject to any disclaimer, the term of this patent is extended or adjusted under 35 U.S.C. 154(b) by 0 days.

(21) Appl. No.: 18/919,029

(22) Filed: Oct. 17, 2024

(65) Prior Publication Data

US 2025/0131992 A1     Apr. 24, 2025

Related U.S. Application Data

(60) Provisional application No. 63/594,316, filed on Oct. 30, 2023, provisional application No. 63/591,395, filed on Oct. 18, 2023.

(51) Int. Cl.
G16H 10/20          (2018.01)

(52) U.S. Cl.
CPC .................................. G16H 10/20 (2018.01)

(58) Field of Classification Search
CPC ........ G16H 10/20; G16H 10/60; G16H 10/40; G16H 15/00; G16H 50/70; G16H 70/20
See application file for complete search history.

(56) References Cited

U.S. PATENT DOCUMENTS

| | | | | | |
|---|---|---|---|---|---|
| 2002/0188475 | A1* | 12/2002 | Banta | ..................... | G16H 10/20 |
| | | | | | 705/3 |
| 2011/0313782 | A1* | 12/2011 | DeMeyer | ............... | G06Q 10/06 |
| | | | | | 705/2 |
| 2013/0159022 | A1* | 6/2013 | Verbeek | ................. | G16H 10/60 |
| | | | | | 705/3 |

(Continued)

FOREIGN PATENT DOCUMENTS

WO     WO-2016187501 A1 * 11/2016     ............. G06Q 10/10

OTHER PUBLICATIONS

Vincent et al., Use of an integrated clinical trial database to evaluate the effect of timing of drotrecogin alfa (activated) treatment in severe sepsis, May 9, 2006, Critical Care, vol. 10, No. 3, pp. 1-10. (Year: 2006).*

*Primary Examiner* — Christopher L Gilligan
(74) *Attorney, Agent, or Firm* — Bookoff McAndrews, PLLC

(57)          ABSTRACT

A method of utilizing data object references to merge one or more programs, the method including: initiating, via a server, a session of a study for a user; assigning, via the server, a first program of the study to the user, the first program including a plurality of events divided into a plurality of phases, generating respective first data objects to reference each event in the first program; receiving a second program for the user, the second program including a plurality of second events divided into a plurality of second phases; identifying a current phase at which the user will enter the second program; generating second data objects to reference each event in the second program that occurs after the current phase; and merging the first program and the second program to determine a merged program.

20 Claims, 8 Drawing Sheets

(56)          References Cited

U.S. PATENT DOCUMENTS

| | | | |
|---|---|---|---|
| 2015/0254432 A1* | 9/2015 | Stumm ............. | G06Q 30/0269 |
| | | | 705/2 |
| 2016/0085943 A1* | 3/2016 | de Vries ................ | G16H 10/20 |
| | | | 705/2 |
| 2018/0060540 A1* | 3/2018 | Caruso ................ | G06F 16/2365 |
| 2020/0265928 A1* | 8/2020 | Hassett .................. | G16H 10/20 |
| 2023/0410959 A1* | 12/2023 | Shah ...................... | G16H 40/20 |
| 2024/0355433 A1* | 10/2024 | Gray ...................... | G16H 10/20 |

* cited by examiner

300

302 ASSIGN FIRST SCHEDULE

304 RECEIVE NEW SCHEDULE

306 IDENTIFY CURRENT PHASE

308 MERGE FIRST SCHEDULE WITH NEW SCHEDULE

1

SYSTEMS AND METHODS FOR UTILIZING DATA OBJECT REFERENCES TO MERGE A PROGRAM

RELATED APPLICATIONS

This application is a non-provisional of, and claims the benefit of priority to U.S. Provisional Application No. 63/594,316, filed on Oct. 30, 2023, and to U.S. Provisional Application No. 63/591,395, filed on Oct. 18, 2023, the disclosures of which are incorporated herein in their entireties.

TECHNICAL FIELD

Various embodiments of the present disclosure relate generally to a scheduler tool, and more specifically to systems and methods for utilizing data object references to merge a program.

BACKGROUND

Generally, clinical studies involve detailed programs for one or more participants. During a study, it may be necessary to update a program of one or more participants. For example, participants may have their respective programs updated in the middle of a program and at various time points. Updating a program for various participants, while efficiently merging events that have occurred with a new program, may be challenging.

Conventional techniques may include programs heavily tied to forms that are built to a particular instance of the program. Edits to the forms may cause data loss or the changing of data types during a study. Another issue with conventional systems is that forms may need to be manually moved and copied from one version of a program to an updated version of the program. This may be inefficient and time consuming.

The present disclosure is directed to addressing one or more challenges such as those referenced above. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF INVENTION

In some aspects, the techniques described herein relate to a method of utilizing data object references to merge one or more programs, the method including: initiating, via a server, a session of a study for a user; assigning, via the server, a first program of the study to the user, the first program including a plurality of events divided into a plurality of phases, generating respective first data objects to reference each event in the first program; receiving a second program for the user, the second program including a plurality of second events divided into a plurality of second phases; identifying a current phase at which the user will enter the second program; generating second data objects to reference each event in the second program that occurs after the current phase; and merging the first program and the second program to determine a merged program, wherein merging the first program and second program includes: identifying and removing all data objects in phases of the first program that have not occurred; and merging remaining first data objects and second data objects.

In some aspects, the techniques described herein relate to a method, wherein the first program includes a document, procedure, or data listing that outlines timelines and procedures for the study.

In some aspects, the techniques described herein relate to a method, wherein the current phase corresponds to a beginning phase, a middle phase, an end phase, an event, an event activity, or a recurring activity.

In some aspects, the techniques described herein relate to a method, wherein the first data objects include: first data reference links connecting the user to a respective event in the plurality of events in the first program.

In some aspects, the techniques described herein relate to a method, wherein identifying a current phase at which the user will enter the second program includes: identifying all phases that have previously occurred in the first program; and identifying a next phase to occur in the first program, wherein the next phase is the current phase.

In some aspects, the techniques described herein relate to a method, wherein identifying a current phase at which the user will enter the second program includes: identifying all phases that have previously occurred in the first program; determining that a user has completed a portion of events in a respective phase of the first program; identifying a corresponding phase of the second program; identifying an anchor point referring to a particular event in the corresponding phase of the second program for the user to begin the second program; and generating second data objects for each event in the current phase of the second program that take place after the anchor point.

In some aspects, the techniques described herein relate to a method, further including: generating and transmitting, to a user computing device, computer-executable instructions configured to cause the user computing device to display the merged program through a graphical user interface of the user computing device.

In some aspects, the techniques described herein relate to a method, further including: identifying a current status for the user, the identifying of the current phase based on the identified current status.

In some aspects, the techniques described herein relate to a system including at least one memory storing instructions; and at least one processor configured to execute the instructions to perform operations for determining data integrity, the operations including: initiating, via a server, a session of a study for a user; assigning, via the server, a first program of the study to the user, the first program including a plurality of events divided into a plurality of phases, generating respective first data objects to reference each event in the first program; receiving a second program for the user, the second program including a plurality of second events divided into a plurality of second phases; identifying a current phase at which the user will enter the second program; generating second data objects to reference each event in the second program that occurs after the current phase; and merging the first program and the second program to determine a merged program, wherein merging the first program and second program includes: identifying and removing all data objects in phases of the first program that have not occurred; and merging remaining first data objects and second data objects.

In some aspects, the techniques described herein relate to a system, wherein the first program includes a document, procedure, or data listing that outlines timelines and procedures for the study.

In some aspects, the techniques described herein relate to a system, wherein the current phase corresponds to a beginning phase, a middle phase, an end phase, an event, an event activity, or a recurring activity.

In some aspects, the techniques described herein relate to a system, wherein the first data objects include: first data reference links connecting the user to a respective event in the plurality of events in the first program.

In some aspects, the techniques described herein relate to a system, wherein identifying a current phase at which the user will enter the second program includes: identifying all phases that have previously occurred in the first program; and identifying a next phase to occur in the first program, wherein the next phase is the current phase.

In some aspects, the techniques described herein relate to a system, wherein identifying a current phase at which the user will enter the second program includes: identifying all phases that have previously occurred in the first program; determining that a user has completed a portion of events in a respective phase of the first program; identifying a corresponding phase of the second program; identifying an anchor point referring to a particular event in the corresponding phase of the second program for the user to begin the second program; and generating second data objects for each event in the current phase of the second program that take place after the anchor point.

In some aspects, the techniques described herein relate to a system, further including: generating and transmitting, to a user computing device, computer-executable instructions configured to cause the user computing device to display the merged program through a graphical user interface of the user computing device.

In some aspects, the techniques described herein relate to a system, further including: identifying a current status for the user, the identifying of the current phase based on the identified current status.

In some aspects, the techniques described herein relate to a non-transitory computer readable medium storing processor-readable instructions which, when executed by at least one processor, cause the at least one processor to perform operations including: initiating, via a server, a session of a study for a user; assigning, via the server, a first program of the study to the user, the first program including a plurality of events divided into a plurality of phases, generating respective first data objects to reference each event in the first program; receiving a second program for the user, the second program including a plurality of second events divided into a plurality of second phases; identifying a current phase at which the user will enter the second program; generating second data objects to reference each event in the second program that occurs after the current phase; and merging the first program and the second program to determine a merged program, wherein merging the first program and second program includes: identifying and removing all data objects in phases of the first program that have not occurred; and merging remaining first data objects and second data objects.

In some aspects, the techniques described herein relate to a non-transitory computer readable medium, wherein the first program includes a document, procedure, or data listing that outlines timelines and procedures for the study.

In some aspects, the techniques described herein relate to a non-transitory computer readable medium, wherein the current phase corresponds to a beginning phase, a middle phase, an end phase, an event, an event activity, or a recurring activity.

In some aspects, the techniques described herein relate to a non-transitory computer readable medium, wherein the first data objects include: first data reference links connecting the user to a respective event in the plurality of events in the first program.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1:
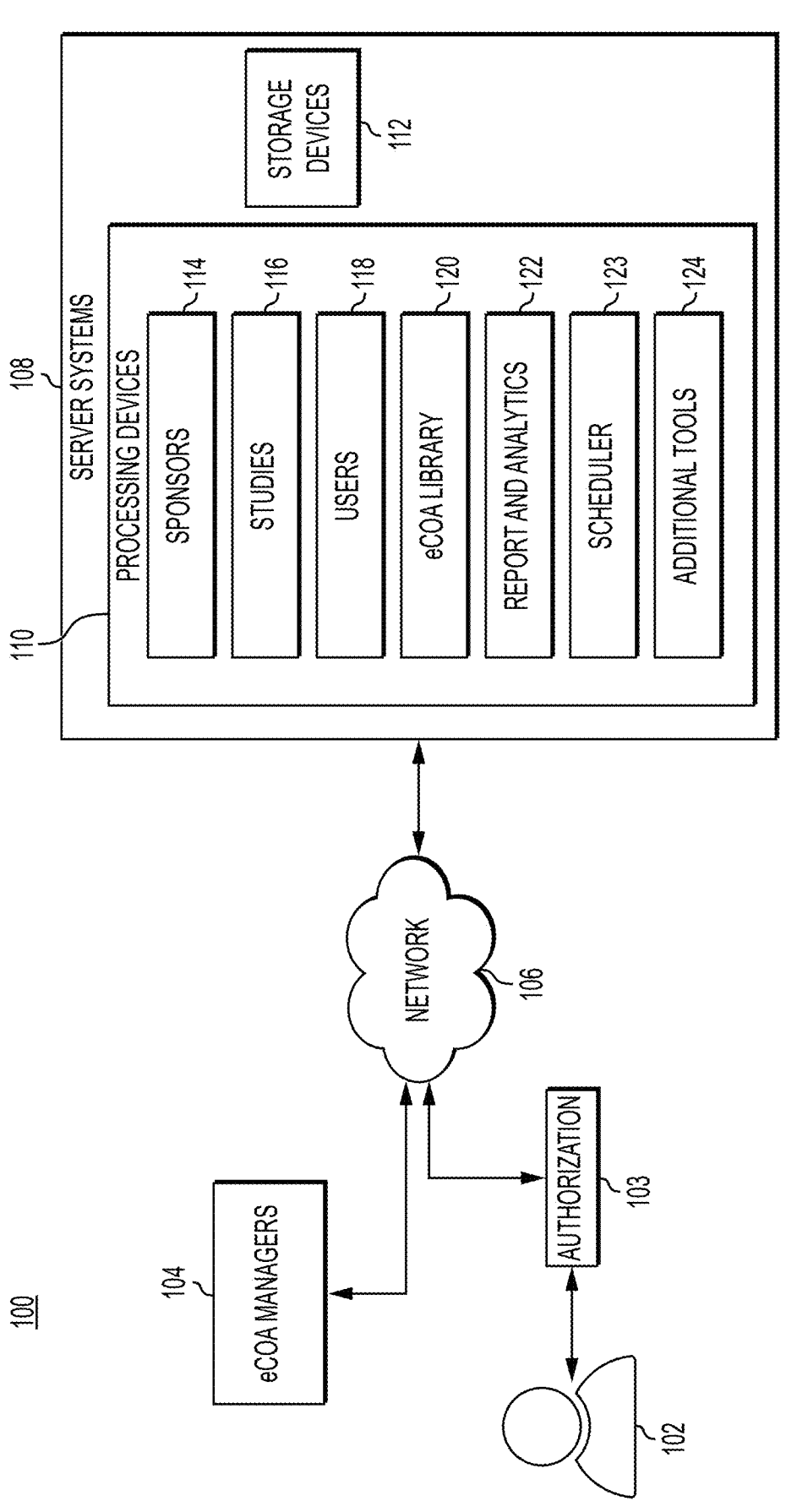
FIG. 1 depicts an exemplary environment for creating, validating, updating, and/or administering an instrument and/or programs, according to one or more embodiments.

Various embodiments of the present disclosure relate generally to a scheduler tool, and more specifically to systems and methods for utilizing data object references to merge a program.

According to embodiments disclosed herein, systems and methods are disclosed for utilizing data object and data object references to merge one or more programs for a clinical trial. A particular clinical trial may have one or more assigned programs for participants within the clinical trial. The program may include phases of the program, planned visits, events (e.g., visit activities) for the patient, and any reoccurring activities. During the course of a clinical study, it may be valuable to update a program for one or more patients, while maintaining all aspects of a program that have previously occurred for a participant of a program. For example, previous data received, such as measurements taken or questionnaires filled out, may need to remain saved and associated with the one or more patients, while the patient's program may need to be updated to reflect planned events of the newly assigned program. The newly assigned program may enable administrators to include additional visits and/or events, or to add events to a schedule that may have previously not been administered.

According to embodiments disclosed herein, the system may initiate a trial session of a clinical program for a participant. A first program of the clinical trial may be assigned to the participant, where the first program has a plurality of events divided into a plurality of phases. Each phases may include program visits and activities for the participant to perform. A set of first data objects may generated to reference each event in the first program. Next, a second program may be created or received. The second program may have one or more updated activities and events programed for the participant. Second data objects may be generated to reference each event in the second program. The system may identify a current phase at which the participant will enter the second program. The current phase may refer to where, in the set of events in the second program, the participant will be placed. A merged first program and second program may be created. The merged program may include all first data objects that have previously occurred in the first program. All first data objects that may not have occurred may be deleted. The merged program may further include the second data object that referenced events that occurred after the current phase of the second program.

Reference to any particular activity is provided in this disclosure only for convenience and not intended to limit the disclosure. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

It will also be understood that, although the terms first, second, third, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Terms like "provider," "medical provider," or the like generally encompass an entity, person, or organization that may seek information, resolution of an issue, or engage in any other type of interaction with a patient, e.g., to provide medical care, medical intervention or advice, or the like. Terms like "patient," "client," "participant," "study participant" or the like generally encompass any person or entity who is obtaining information, seeking resolution of an issue, or engaging in any other type of interaction with a medical provider, e.g., to receive such care, information, or the like. Terms like "user" generally encompass any person or entity that may obtain information, resolution of an issue, purchase of a product, or engage in any other type of interaction with a provider or patient, whereby the user may be the medical provider or the patient as the case may be. For example, an individual that collects data on themselves may be both a patient and a user. A user may also refer to a patient that is being assisted by a provider. Further, a user may refer to a provider entering data on behalf of a patient.

In some instances, implementing a clinical trial to conduct clinical research may include having standardization of clinical endpoints. The clinical endpoints may include outcome measures of clinical research trials. Clinical endpoints may include instruments or artifacts. An instrument or artifact may refer to an assessment that has been developed that has been shown to provide clinical meaningful outcomes based upon a certain change from the baseline of a participant. An instrument may contain specific structure and may be configured to be displayed in a manner specific to an author's intent and/or clinical trial guidelines or regulations. An artifact may include any other material or item with textual content that may be provided as part of a clinical trial. While examples and embodiments below may reference an instrument or an artifact, it should be understood that the techniques disclosed herein may be adapted to either, as well as to any other suitable textual content.

An exemplary instrument may be a questionnaire such as an electronic clinical outcome assessment ("eCOA"). An eCOA may need to be validated clinically to support regulatory submissions. Clinical validation may be a process of verifying an instrument's procedures (e.g., the set of questions) to verify that the measurements provide a clinically meaningful outcome. A clinical validation may, for example, be performed internally by a particular organization. A clinical validation may be constructed to be standardized for a validated instrument (e.g., such as a validated eCOA). A clinical validation may promote the use of a standard set of data from time point to time point and provide reliable results with a known outcome that is based upon a change over time as opposed to a random error.

The process of creating, validating, and using an instrument (e.g., an eCOA) may be time consuming. For example, the process of performing a clinical validation may take multiple months for a single eCOA to be created and validated.

Conventional systems for clinical studies may require validating an instrument for each particular study. An issue may arises that when a new study wishes to utilize a previously created validated instrument, then the instrument may need to be revalidated. Further, if a study is translated, further validations of each translation may need to be performed. For instance, context for language may affect its understood meaning, and thus even minor changes due to translation may have an impact on the way in which a reader will understand or respond to the content. In order to ensure that such variation does not materially affect the outcomes of a trial, separate validation of each translation may be required. This process may be time-consuming and waste resources for new studies. In conventional studies, questionnaires and forms may be created in each specific locale and then served to patients. This may include one or more of the following three problems: (1) only the participant's native language can be seen by the physician and the clinical staff; (2) all results are saved in the participant's native language; and (3) when reporting the saved response, it is necessary to convert the native language to a common language.

One or more embodiments of the system described herein may provide a digital platform that has the means to configure a clinically validated instrument, create screen shots for verification from the author, and store a digital version for use without changing the underlying structure of the validated instrument. The digital platform may include digital storage of an instrument, certification of validations of an instrument, translations of a particular instrument, screen shots of a particular instrument, and means to utilize a digital store for an identical representation of a validated instruments for one or more studies.

One or more embodiments of the system may offer the advantage of only requiring a single configuration of an instrument. For example, the system may offer tools to create and store a particular eCOA within the platform. The system may offer the advantage of requiring only a single validation of a created instrument. This instrument may be accessed and utilized in multiple studies while staying validated, as will be described in greater detail below. The system may offer a single certification of an instrument. If the system utilized separate instruments for each respective language, then each instrument would need to be validated or certified. This would increase the complexity, cost, and time for conducting a clinical study. Certification as used herein generally encompasses a process by which an instrument undergoes a technical validation that it conforms to an author's original electronic or paper version according to the author's wishes. This technical validation process, in embodiments, may be separate from a clinical validation of the instrument (i.e., confirming that endpoints are statistically significant), and instead refers to the verification that the look and interpretation is as the author intended with the original validated instrument.

One or more embodiments of the system may offer tools for a participant and/or an organization to prepare an eCOA. The system may further offer tools to create a study, as well as a program that utilizes a validated eCOA. A study may refer to a research study involving human subjects that aims to evaluate the effects of a biomedical intervention (e.g., drugs, treatment, devices, etc.) on health-related outcomes. A program may refer to a program of activities that provides the tasks and milestones, along with the corresponding timeline that are critical to the execution of a study.

One or more embodiments of the system may offer a digital platform that utilizes a method for using data reference links to maintain data validation during use. As will be discussed in greater detail below, a validated instrument may be accessed for a trial session during a study. The system may allow for the transmission of a request for a particular instance of a validated instrument during the trial session. The system may be configured to receive a data reference object that is operable as a data reference link to the validated instrument that is stored in an instrument library, such that the data reference object is operable to execute the validated instrument without generating a copy of the validated instrument. The system may further allow for a Graphical User Interface ("GUI") of the trail session to operate the data reference object, such that the participant device executes the validated instrument by reference.

During a clinical trial, it may be necessary to update the program of one or more participants. Traditional systems may perform this function by creating entirely new protocols or programs and transferring all data to the newly created protocol. This may be time consuming and inefficient. In an example, this may involve attempting to determine a correspondence between events in a new program and events in a previous program. Not only can this be a labor-intensive process, but that correspondence may not be available. For instance, a patient may have had two visits in the past, while a new program they are being moved to only has one visit in that time period, and thus it may not be possible to draw a direct correspondence. Since conventional scheduling solutions use identical programs for each participant in a study, this type of misalignment may complicate program updates and/or transfers, and result in artifacts (e.g., a "missed visit") or incomplete transfer of patient data.

One or more embodiments of the system may include a scalable and flexible study scheduler. The scheduler may align with the Program of Activities (PoA) per the clinical trial protocol. The scheduler of the system described herein may accommodate one or more PoA per study and multiple form versions utilized per program. The scheduler may be designed to enable loose references (e.g., to data objects) to events within a program (e.g., within the PoA). This system may enable a single form to be utilized by more than one program simultaneously. This may allow for the development and verification of a single form that can be shared by multiple PoAs.

One or more embodiments of the system may further include techniques for modifying a program of a participant. For example, the system described herein may be configured to combine one or more program while a clinical study is being conducted. The system may, upon initiation of an update to the program, perform a stitching procedure to generate a hybrid program that combines a new program's remaining or future content with all previously conducted or past aspects of a current program. This may enable the program for one or more participants to be updated at varying points in a program. The stitching of programs may thus be performed on a per person basis, so the new program can be implemented for each person based on their current progress in the original program. Further, since past aspects of a program are preserved, there may be less need to determine correspondence between programs when serving updates. In an example, once an anchor point in a new program, e.g., a point in the new program corresponding to a current point in time or stage in the current program, is determined, no additional correspondence may be needed.

FIG. 1 depicts an exemplary environment 100 for creating, validating, and administering an instrument, according to one or more embodiments. Environment 100 may further be configured to mere one or more scheduled assigned to a user 102 as described in greater detail below. Environment 100 depicts an electronic network 106 that may facilitate communication with one or more eCOA Managers 104 (e.g., an administrator role that allows a user to manage eCOAs and schedules), users 102, and/or a scheduled 123. As used herein, an eCOA manager 104 may include or be associated with a server configured to interact with the server systems 108 described below. The eCOA manager 104 may be responsible for creating, certifying, and/or validating instruments for one or more studies. An eCOA manager 104 may further be utilized to create a study as well as a program for a study. The eCOA manager 104 may further include a trial server to initiate a trial session of a clinical study for one or more users 102.

Further, a user 102 may access one or more instruments through the network 106. A user 102, may for example be a patient (e.g., a participant) participating within one or more studies. The user 102 may be assigned to a trial session of a clinical study, where the clinical study includes a program. The program may refer to a schedule of activities that provides the tasks and milestones, along with the corresponding timeline that are critical to the execution of a study. The user 102 may, for example, access an eCOA or their respective program for a particular study through a graphical user interface (GUI) of a user device. The user device may be a computing device such as computer 700 described below. This may allow a user 102 to respond to and answer questions for a particular eCOA. The eCOA forms may be located in an eCOA library 120 of a server systems 108 as will be discussed in more detail below. When a user 102 accesses the system described herein, a unique token may be created that allows for the system to uniquely identify the user 102. The token may include metadata (e.g., in the standard of ISO 639-1 standard language code) of the respective user's 102 preferred language.

A user 102 may require an authorization from an authorization system 103 prior to accessing an eCOA form. For example, a user 102 may first require permission to access eCOA forms. As will be discussed in further detail below, eCOA forms as well as programs may be stored in a fast healthcare interoperability resource ("FHIR") server. FHIR may refer to the set of rules and specifications required for exchanging electronic healthcare data. To access the FHIR server, the user 102 may utilize an authorization system 103, as the FHIR server may not be accessible directly from the internet. The authorization system 103 may include an identity provider ("IDP") web server that allows access to the FHIR server in which the eCOA forms and programs are stored. The authorization system 103 may further include a firewall and a particular application programming interface ("API") (e.g., an Azure API for FHIR) for accessing the eCOA forms or programs stored in the eCOA library 120 or storage devices 112.

A user 102, e.g., a participant, administrator, or the like, either at a clinical site or remotely may utilize a computing device (e.g., computer 700) to obtain access to a particular study. The computing device may be represented as a "client-side caller" device. This device may identify whether the participant has access to a particular study service, e.g., by performing a permission call. Permission may refer to an identifier for resources that client wants to access. The permission call may have access to a local device conducting a study. The local device may for example have access to server systems 108.

According to an exemplary embodiment of the present disclosure, the electronic network 106 may also be connected to server systems 108, which may include processing devices 110 that are configured to implement one or more modules or servers (e.g., sponsors module 114, studies module 116, users module 118, eCOA library 120, report and analytics module 122, scheduler 123, and additional tools 124) configured to create, certify, validate, administer, and or store one or more instruments for use within a study, according to an exemplary embodiment of the present disclosure.

The sponsors module 114 may be configured to store information related to a sponsor utilizing the server systems

108 to conduct a study. For example, the sponsors module 114 may keep track of organizations that are utilizing the server systems 108 to conduct a study. The sponsors module 114 may track each sponsor's studies, plans, and any created instruments by the particular sponsor.

The studies module 116 may include a database tracking all active and past studies performed by the server systems 108. The database within the studies module 116 may include, for example, a protocol number, a study name, a corresponding sponsor, a configuration status, and any pending actions for any studies conducted by the server systems 108. A moderator for a study may access the current results of a study through the studies module 116.

A users module 118 may be configured to store information related to patients of a study, study personnel, and system administrator. The users module 118 may further include any studies the user is participating in. The users module 118 may further include a user's full name, language(s) spoken, email address, role within the system, account status, and last login into the system described herein. Further, the users module 118 may be configured to add additional users to one or more studies. For example, an eCOA manager 104 may enter the email address, name, language, time zone, role, assigned study, and assigned site of a new user to the users module 118.

The eCOA library 120 may be configured to store one or more instruments including an eCOA. The eCOA library 120 may store the title, type of instrument, status of the instrument, amount of external version, amount of internal versions, and allow for actions to be conducted regarding an instrument. The eCOA library 120 and/or documents within the eCOA library 120 may be stored in a Fast Healthcare Interoperability Resource (FHIR) server. The eCOA library 120 may further include a "new form" function. The new form function may allow for an individual (e.g., an eCOA managers 104) to create a new eCOA form. For example, the interface may allow a user to create a display type, questions types, and sliders for a particular study. Question types may include the number, quantity, date, time, text, choice, and EuroQol (EQ)-visual analogue scale (VAS). The eCOA library 120 may further be configured to store a translation key, the translation key defining an arrangement of source text within a validated instrument.

The reports and analytics module 122 may be configured to store one or more reports and or analytics corresponding to one or more studies from the studies module 116. The reports and analytics library may include one or more data analysis tools to further analyze, graph, and organize responses to the instruments from the eCOA library 120. Further, reports may be generated that include the analysis and graphs performed. The analytics and reports may for example be accessed by the eCOA managers 104.

The scheduler 123 may be configured to facilitate the design and scheduling of programs. For example, the server systems 108 may accommodate one or more PoA's for one or more clinical studies.

When preparing a PoA for a clinical study, there may be specific clinical and participant data points that are to be captured for a given protocol version of a clinical study. Each program may be unique and require particular forms to be created to capture the data. Answers and updates to a form both prior to and during a study may be desired. For example, there may be protocol amendments prior to a first participant being enrolled in a study. The scheduler 123 may be configured to enable a loose reference (e.g., data objects) to particular events of stored forms within the PoA (the PoA being stored in the server systems 108). This may enable the same form to be utilized by one or more programs simultaneously. This may enable the development and verification of one form that can be shared by many PoAs. An PoA can be copied to make a new PoA and reference the identical forms that were used by an original PoA, while not creating a clone of the original form. As the form is unchanged, there may be no need for regression tests of the new forms.

The scheduler 123 may further include saved programs to be accessed by a participant in a clinical study. For example, a program may include a set of phases, wherein each of the set of phases has one or more events. The system described herein may link, using data objects, a particular participant to respective events of a program. The data objects may be created based on a participant being assigned to particular clinical study. These data object may be removed and created within the scheduler 123. The scheduler 123 may be configured to generate new data object links to new events added to a program. The scheduled 123 may further, upon notice that a participant has been assigned a new or updated program, delete data objects for events that have not occurred and create new data objects to a new or updated program. When a participant is assigned a new or updated program, the previous program may not be deleted, but merely data objects to events that have not occurred may be deleted. This may allow for all previous events and corresponding metadata to the events to stay saved for a participant when a program is updated.

The scheduler 123 may, for example, be configured to generate, edit, update, and/or combine a created program for one or more participants. For example, a clinical trial session for one or more participant may be initiated. The clinical trial session may refer to the process and systems for a particular participant to follow and complete a program, where the program refers to a document, procedure, data listing, or the like that outlines the timelines and procedures for a clinical trial. A particular program may include a set of activities (i.e., events) as described below in FIG. 2. The one or more participants may proceed with following the program at different time intervals. The clinical trial session may, for example, be initiated by an eCOA manager 104 accessing an electronic network 106 in order to allow a user 102 to access a program. The clinical trial session may be initiated within the processing devices 110 of FIG. 1.

During the trial, the program may be accessed by a participant or an eCOA manager 104. The program may be accessed by one or more data object, where the data objects may include a reference or pointer to a respective event of a program. The scheduler 123 may be configured to allow for the editing and/or updating of a program by an administrator. The system may be configured to enable the program to be updated even as one or more participants is mid trial.

The scheduler 123 may be configured to create one or more new custom program data object upon initiation of a new or updated program mid trial. Upon receiving a request for an edit or update, the scheduler 123 may first receive an input, an edit to a program, or a new program to follow. The scheduler 123 may further be configured to identify all aspects of the program that have been complete for each of the one or more participants for whom the edit or updated program is applicable to. This may be participant dependent. Upon finding the current completion point in the study, a portion of the current program prior to that current completion point may be identified. The data object pointing to future events that have not occurred for a study may be deleted.

The scheduler 123 may be configured to determine where in the newly received program to have the one or more participants resume operations, e.g., an "anchor point" for the newly received program to take over from the current program. The scheduled 123 may further be configured to identify a current phase representing the phase of the new program that a participant should resume in. For example, this may be input manually by a participant. In another example, the system may compare the programs based on events and align the activities of the old program to the new program. The system may then determine a current phase and/or an anchor point in the new study, corresponding to where the new study should begin in progress for the one or more participants. This determination may be based upon reviewing and matching event that have previously occurred in the old study to corresponding events in the new study. In some cases, the anchor point may be in between phases of a particular study. In other cases, the anchor point may be in the middle of a study.

The scheduler 123 may enable a single form to be constructed through a set of data objects referencing events from one or more programs. The single form may be named and assigned to a particular program of a clinical study. Further, the form may be reviewed and validated within the server systems 108. The single form may be deployed within a particular study in multiple manners by referencing the created form through separate data objects. A server systems 108 may enable a user (e.g., the eCOA manager 104) to program from development to quality assurance (QA)/user acceptance testing (UAT) to all within the same configuration workflow. For example, the system may be set up to allow a "status" to be utilized that prevents the building, exporting, and rebuilding of a program/study on multiple servers. Therefore, the tested study may be the study that goes "live." This may allow for a single round of testing and deployment. Once a program is deployed, a user (e.g., a eCOA manager 104) may utilize the scheduler 123 to clone the program, make necessary changes (add/remove forms) all without making changes to the underlying data and database. Effectively, one may test the program and changes made to the program, not the prior referenced forms, making the system more accurate and highly scalable. Study program changes may be implemented without sacrificing prior submitted data integrated, as impacted forms/programs are transactional and do not require database changes.

The additional tools 124 may include one or more processors or servers configured to perform function such as: developing a study, a study configuration, translations, sites, tokenization, and resources. Study configuration may refer to the phases, visits, recurring questionnaires, and their association with each. Configuration may refer to "how" instruments are assigned in a specific program for a participant or clinical site to complete the questionnaire. The execution of the study program may refer to "when" each of the events (e.g., questionnaires) will occur. The study configuration may include a calendar of the particular events. Sites may refer to the clinical sites that are defined for each study. Each site may have one or multiple languages assigned to the configuration. The developing a study function may allow for a user to upload planned medical tests and measurements, as well as a particular timelines for all parts of the clinical study. Once a study is created, a participant (e.g., an individual administering or creating the study) may assign a timeline for each phase of the study.

One of the additional tools 124 may enable translations of the study. In conventional studies, questionnaires and forms may be created in each specific local and then served to patients. This may include the following three problems: (1) only the participant's native language can be seen by the physician and the clinical staff; (2) all results are saved in the participant's native language; and (3) when reporting the saved response, a system must convert the native language to a common language. In contrast, the system described herein may perform the following three steps: (1) administer the instrument (e.g., the eCOA) in a language native to the participant and allow the participant to complete the study in their native language; (2) translates (e.g., by a third-party translation service) the response back to a common language prior to the study team reviews the results; and (3) the results of the questions are saved in a common language for reporting, which may assist with regulatory submissions.

One of the additional tools 124 may further include the ability to provide a preview element for an eCOA manager 104 preparing an instrument. This may enable a configurator to render an emulated version of a clinical eCOA without deploying it to a separate environment and loading it into a mobile device. This may expedite the process of developing a an instrument. A problem with conventional clinical questionnaires is that a portion of the process for preparing questionnaires is to render and review screen shots of the instrument. This may be cumbersome as the instrument must be deployed to an environment and rendered on the mobile device multiple times before getting spacing, text, and font completed to the author's specification. The system described herein may offer one or more of the following three advantages as compared to conventional systems: (1) configured screen can be reviewed for accuracy, completeness, and overall design without leaving the configuration tool during construction of an instrument; (2) screen shots can be taken via the tool to reduce the need for one-by-one screen shots rendered on a mobile device; and (3) configuration may become quicker without deployments to a separate environment for verification. Advantage (2) may take effect during the certification process of an instrument, and subsequent submission to an internal review board. In some instances, one or more screen shots of each instrument may be required as evidence of the representation of the instrument on a mobile device. Each screen shot may then be used to confirm the instrument conforms to the standards set by the author and does not coerce or lead the participant in any way based upon the layout, button placement, etc. Overall, this feature may assist with expediting the process of creating an instrument.

The server systems 108 may further include one or more storage devices 112. The storage devices 112 may be responsible for storing uploaded instruments, studies, clinical trial information, user information, reports and analytics, as well as sponsor information. Each of the modules within processing devices 110 may have access to the one or more storage devices 112.

Any of the above devices, tools and modules may be located on a device that may be connected to an electronic network 106, such as the Internet or a cloud service provider, through one or more computers, servers, and/or handheld mobile devices.

Figure 2:
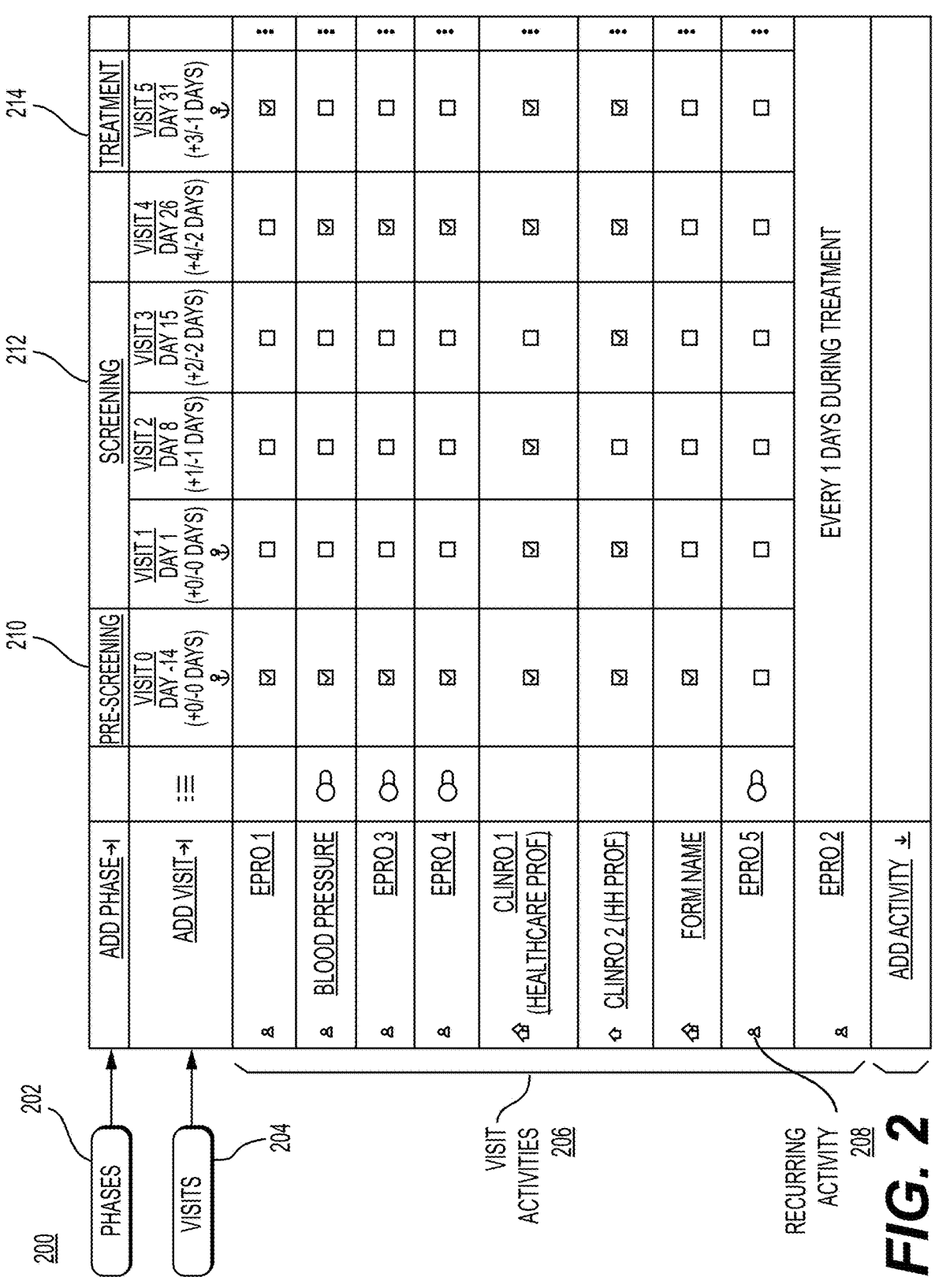
FIG. 2 depicts an exemplary program, according to one or more embodiments.

FIG. 2 depicts an exemplary program 200, according to one or more embodiments. The exemplary program 200 may include a set of phases 202 representing particular phases of a program for a clinical trial. For example, the phases 202 of the exemplary program 200 may include a pre-screening phase 210, a screen phase 212, and a treatment phase 214. In general, phases of a study may be associated with a beginning phase, a middle phase, or an end phase. The pre-screening phase 210 may be a beginning phase, the screen phase 212 may be a middle phase, and the treatment phase may be an end phase of a study.

Each respective phase may include a visit 204. A visit 204 may be to a clinical site (such as a hospital, medical facility, testing facility, facilities conducting a study, etc.) or virtual (e.g., accessed through a computing device). Each visit 204 may have a set of activities 206 associated with a visit such as meeting with a health professional. The activities 206 may be considered "events" for the participant of a study. Further, studies may have recurring activities 208 (e.g., reoccurring events) that may occur either: at set time intervals (e.g., every day, every week, or every month) . . . . Recurring activities 208 may need to be completed by the participant on a regular schedule (e.g., every day at 8:00 AM). An exemplary recurring activity may be filling out a questionnaire related to the study at set intervals (such as an EPRO 5 form). In some examples, each activity 206 may be associated with a questionnaire that must be completed by either the participant or a healthcare professional. Exemplary activities 206 may include filling out questionnaires, recording medical measurements and/or readings, (e.g., blood pressure) etc., The checked boxes of program 200 may refer to which activities occur for particular visits 204 for a clinical trial.

When a program 200 is assigned to a particular participant, dates may be assigned for the visits 204. The dates assigned may be required to fit in a scheduled timeline, such as within a time window using pre and post offsets, where specific dates are scheduled when a participant is assigned to a clinical study. For example, visit 14 may be assigned to a date that can be anywhere from the $24^{th}$ day to the $30^{th}$ day of a program as it was assigned a +4/−2 days of the day 26 window. Dates may be assigned automatically upon a participant being assigned to program of a clinical study. In some examples, a participant may select dates to perform activities that fit within set timelines assigned for each visit or event.

Other programs, such as new or updated programs that may be received for a clinical study, may include additional visits or activities. For example, a first program may not have all optimal activities for a particular clinical study. In another example, a first program may have had a missed activity. A new program may be generated to include additional or missed activities. The new program may then be me merged with the previous program and assigned to a participant of the study. When a new program is received, if various participants require the new program, each participant may receive a participant specific merged program that merges the first program with the second program depending on each participant's progress through the first program. This may work as each participant may be assigned a set of data object that reference the events of the first program. When a second program is received, each participant may have all data objects to upcoming events from the first schedule removed. Further, a current phase and/or an anchor point may be determined to identify what events in the first program have been completed for each participant. A current phase and potentially an anchor point may be identified where each participant may enter the second program. New data objects may be generated referencing each participant to the respective events of the second program that take place after the current phases and/or anchor point in the second program. This may mean that if a clinical trial with multiple participants receives a new or updated program, each participant's specific program may be updated individually based on that participant's progress in the study. Further, both the first program and second program may remain saved in the system, and only data object with references to specific events of the first and second program may be created and deleted.

Figure 3A:
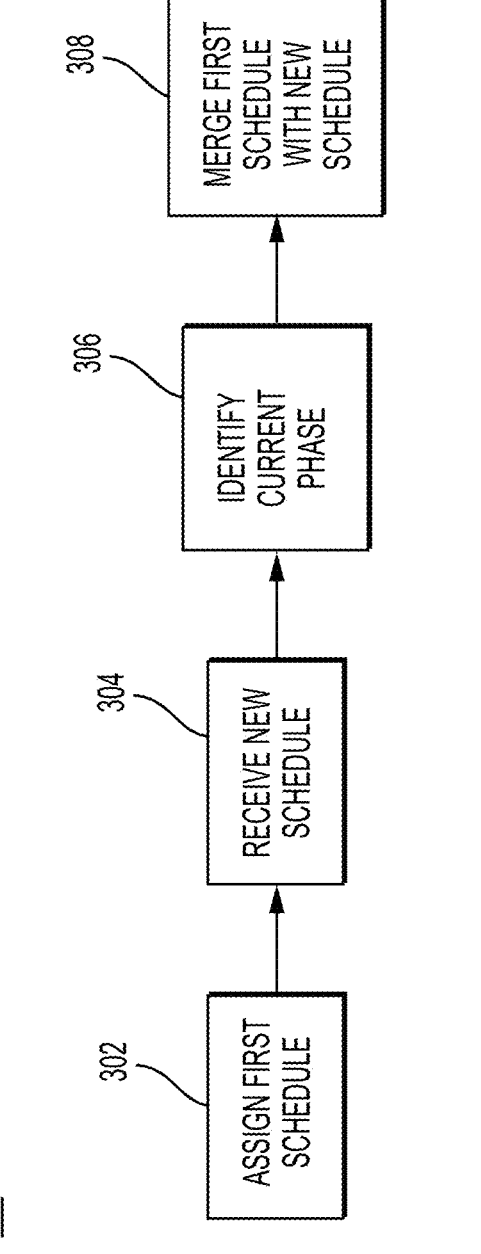
FIG. 3A depicts an exemplary flow diagram depicting the merging of a first and second program, according to one or more embodiments.

FIG. 3A depicts an exemplary flow diagram 300 depicting the merging of a first and second program, according to one or more embodiments. The flow diagram 300 described in FIG. 3A may be performed by the environment 100 of FIG. 1. In other examples, aspects of the flowchart described in FIG. 2 may be performed in external systems and received by the environment 100. Alternatively, the flow diagram described in flow diagram 300 may be performed by any computer process system capable of administering instruments such as computer 700. Moreover, it should be understood that, in various embodiments, various steps may be added, removed, or rearranged.

A trial session of a clinical study for a participant may be initiated via a trial server. At step 302, a first program of the clinical study may be assigned to the participant. The first program may include a plurality of events divided into a plurality of phases. Phases of a study may be defined as periods of time where one or more events may occur. For example, the program may include a beginning phases, a middle phase, and an end phase referring. The beginning phases may include events such as initial data measurement of a participant such as samples and readings of a participant. The beginning phase may further include initial surveys and forms completed by a participant. The middle phase may include events that take place during patient screening, and/or treatment or intervention events that may be administered to a participant. The end phase may include events such as forms, questionnaires, additional measurement, samples, and reading from a participant. Each phase may include one or more visits. A visit may include one or more events or activities to take place. A visit may occur in person at an organization site that may include medical equipment to administer the collection of samples, reading, etc. The organization site may further be for collection of forms. In another example, the visit may be may be administered in a remote fashion (e.g., a tele-visit) across a large geographical area. In another example, the visits may include a healthcare professional visiting in person to the participant's location to administer one or more activities. In some examples, each event may have a corresponding questionnaire that needs completion.

Step 302 may further include generating respective first data objects to reference each event in the first program. For example, each data object may include a data reference link connecting the participant to a respective event of the first program. The first data objects may include metadata indicating a proposed date for the event if it has not occurred and a date of occurrence if the event has occurred. Further, upon the particular event occurring for the participant, related data from the event may be saved and associated with the data object (e.g., results to a question are filled out). In an example, if blood samples are taken at a particular event, the results may be saved for the participant at the particular data object. For example, readings, measurements, questionnaires, samples, etc. may be uploaded by a participant, clinician, study administrator, doctor, etc. and associated with the metadata data of a first data object upon the respective event associated with the first data object occurring.

Step 304 may include receiving a second program for the participant. For example, the second program may be a new or updated version of the first program. The second program may be administered for all participants of the clinical study. The second program may include a plurality of second events divided into a plurality of second phases. For example, the second program may further include a beginning phase, a middle phase, and an end phase.

Step 306 may include identifying a current phase at which the participant will enter the second program. In some cases, step 306 may further include identifying an anchor point that refers to an exact event in the second program that a participant may switched to the second program. An anchor point may be identified when a participant's schedule is merged while in the middle of completing a particular phase. Step 306 may include identifying all phases that have previously occurred in the first program; and identifying a next phase to occur in the first program, wherein the next phase is assigned as the current phase. This may be obtained by searching all data objects for metadata establishing whether a particular event was completed.

In another example, step 306 may include identifying all phases that have previously occurred in the first program; determining that a participant has completed a portion of events in a respective phase of the first program; identifying a corresponding phase of the second program; and identifying an anchor point referring to the particular event in the corresponding phase of the second program for the participant to begin the second program. In this example, the anchor point may refer to as the particular event in the corresponding phase of the second program where the participant will begin. The anchor point may be determined by matching all event from the current phase of the first program to all events of the current phase of the second program. Next, a set of matched events that has previously occurred (e.g., the respective metadata for the first event is completed) may be identified. An earliest or first occurrence of either (1) a matched event that has not occurred in the first event, or (2) a new event now in the second program may be identified. This earliest time point and respective event may be assigned the anchor point.

In an example, a study may be sub-divided into various phase. A current phase for a patient may be identified. The current phase may be used when determining the anchor point in an updated or new program. For instance, a current phase X in the first program may correspond to stage Y in the second program, such that the space for comparing the programs to find the anchor point may be reduced down to just stages X and Y, rather than an entirety of the programs. In an example, in some circumstances, it may be beneficial for a patient to finish a current phase before executing a program change or update. In an example, the system may limit or select an anchor point accordingly. In an example, the system may identify future events in the current program for the current phase of the study, and evaluate identified events when determining the anchor point.

Upon identifying the current phase, the method may further include generating second data objects to reference each event in the second program that occurs after the current phase and/or after the anchor point.

Step 308 may include merging the first program and the second program to determine a merged program for the participant. This may include, identifying and removing all data object in phases of the first program that have not occurred; and merging remaining first data objects and second data objects. Upon the merger, the merged program may include data objects from both the first and second program. The merged program may include all saved metadata and associated data from the first data objects referencing events that occurred in the first program.

The method of FIG. 3A may further include generating and transmitting, to a participant computing device, computer-executable instructions configured to cause the participant computing device to display the merged program through a Graphical User Interface (GUI) of the participant computing device. For example, this output may look similar to the program 200 of FIG. 2. This may allow a participant or individual associated with a study to view a merged study and review any associated metadata corresponding to events of the merged program.

The method of FIG. 3A may further include identifying a current status of the participant after the merged program has been determined. The current status may identify the current phase, or non-phase status, the non-phase status being hold, withdrawn, or opt-out. If use was previously associated with a non-phase status, such as hold, withdrawn, op-out, screen failure the participant may be left in that status. If not, if the current day in the schedule that the participant is in falls on the same phase as the prior schedule that has been activated then the participant will be left in this status, otherwise their status will be set to hold.

Figure 3B:
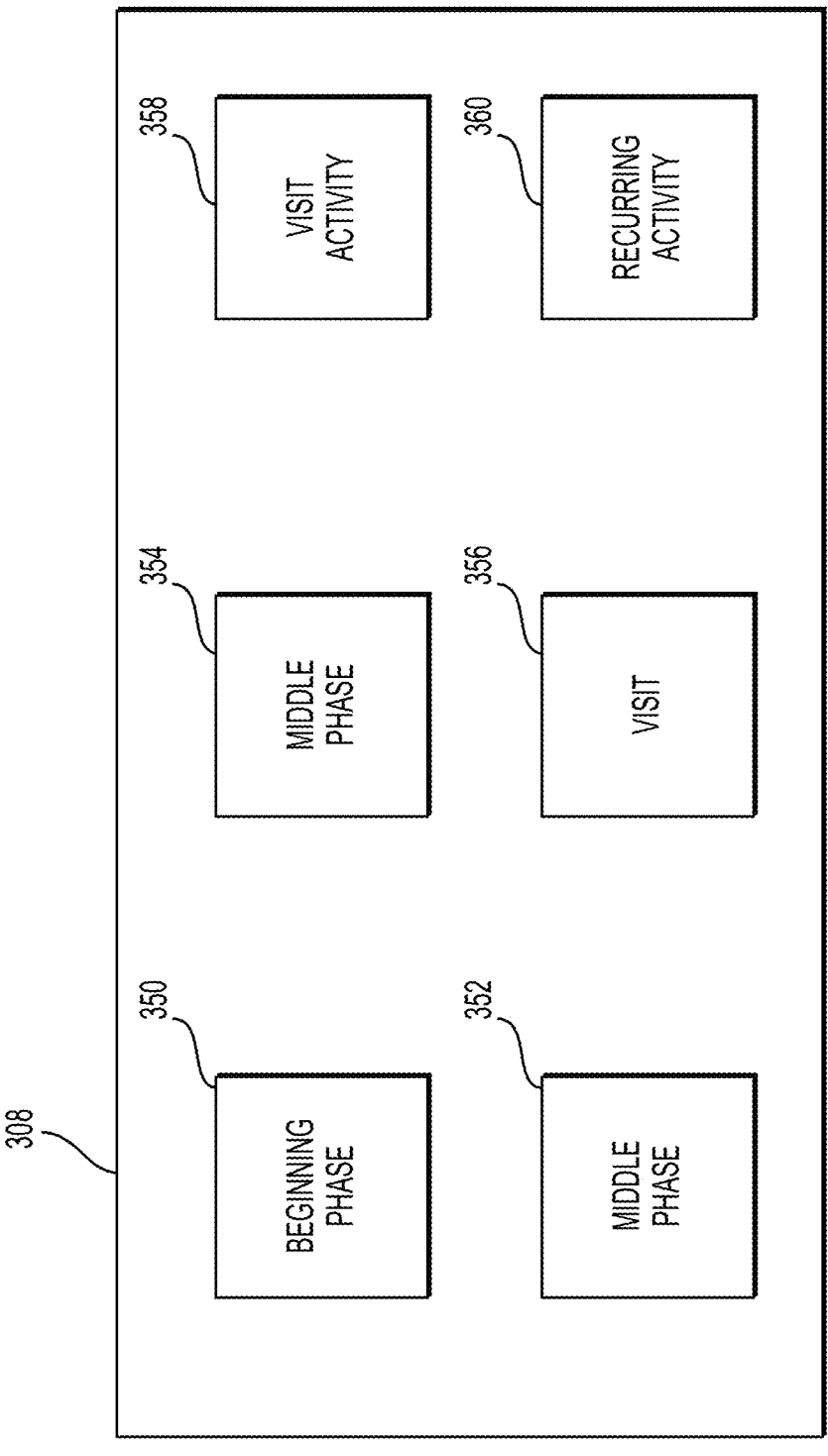
FIG. 3B depicts an exemplary diagram of various scenarios that include merging a program, according to one or more embodiments

FIG. 3B depicts an exemplary diagram of various scenarios when merging a program, according to one or more embodiments. For example, diagram may illustrate various scenarios that a participant may be in when a participant's study is merged according to FIG. 3A. For example, these scenarios may be identified at step 306 of FIG. 3A.

If at step 306, the participant's current phase is identified as in the beginning phase 350, middle phase 352, or end phase 354 the following may occur. First, the first program may be analyzed. All events that have already occurred in the current phase of the first program (e.g., in any of the beginning phase 350, the middle phase 352, or the end phase 354) may be identified. Further, all event that occurred in any preceding phases may be identified. The data objects referencing these events that have occurred may be kept and continued to be saved data reference links to the events. All remaining data objects associated with the first program that take place in the future may be deleted (both from within the phase and in future phases).

Next, the second program may be identified. The identified phase may first be examined. All phases that take place prior to the current phase may considered irrelevant. New second data objects may be created and reference all events in the future phases of the second program. For example, if the current phase is identified as after the beginning phase 350, then all events from the middle phase 352 and end phase 354 may have data objects created to reference the respective events of the second program.

If an anchor point is determined in the middle of one of the respective phases, the following may occur. All events from the current phase of the first program may be identified and matched to events from the current phase of the second program. Data objects may then be created for the events of the current phase of the second program if either (1) the matched event from the first program has not previously occurred, or (2) a particular event of the current phase was not scheduled in the first program.

In an example scenario 356, a visit with a set of events may be added or updated in the second program. Similar to above, if all events of the visit have occurred these events may stay saved for the merged program. If the events of the visit are all new or have not previously occurred, then new data objects may be assigned to all events of a newly assigned visit. This may effectively add a visit to a participant's respective merged program of the clinical trial.

In an example scenario 358, a visit activity (e.g., event) may be added or updated for a particular visit. Similar to above, if the visit had previously occurred, no action may be needed for the merged program, however, if this visit has not occurred, then a new data object may be created to reference the new or updated visit activity. If the visit activity is an update (as opposed to a new activity), the previous data object referencing the now irrelevant visit activity may be deleted (assuming the visit activity has not yet occurred).

In example scenario 360, a recurring activity may be added to a second program. If the recurring activity also existed in the first program, then new data objects may be created to reference the recurring activity for the future. If this recurring activity starts in the future (e.g., after the current phase) then all of the scheduled activity instances will be added to the schedule. If the recurring activity is scheduled to start in the past but ends in the future then all the future instances of this activity may be added to the schedule (e.g., by data objects).

For scenario 360, if the recurring activity may not have existed in the first program, then all future activities may be added to the merged program with new data objects. For scenario 360, if a first program included a recurring schedule and the second program did not include this, then all references to future occurrences of the recurring activity may be deleted, while the data objects referencing already occurred versions of the activity may be maintained.

Figure 4:
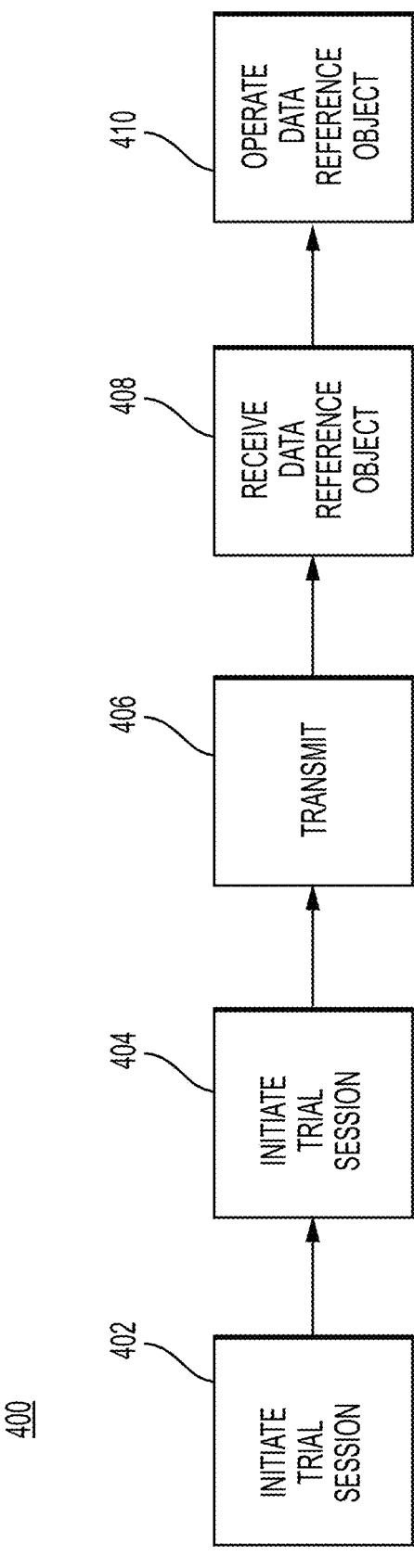
FIG. 4 depicts an exemplary flow diagram illustrating a workflow for obtaining an instances of a validated instrument, according to one or more embodiments.

FIG. 4 depicts an exemplary flow diagram illustrating a workflow for obtaining an instances of a validated instrument, according to one or more embodiments. The flow diagram described in FIG. 4 may be performed by the environment 100 of FIG. 1. In other examples, aspects of the flowchart described in FIG. 4 may be performed in external systems and received by the environment 100. Alternatively, the flow diagram described in flowchart 400 may be performed by any computer process system capable of receiving image inputs such as computer 700.

At step 402, a trial session for a participant may be initiated. A trial session may refer to the process and systems for a particular participant to complete an instrument associated with a particular clinical study. For example, a trial session for a participant may be initiated once the participant has completed a portion of a clinical study. The trial session may be initiated by a provider of the clinical study. The trial session may be initiated to help standardize a clinical endpoint to meet specific measures set forth to support changes in reported data. The trial session may for example be initiated by an eCOA manager 104 accessing an electronic network 106 in order to allow a user 102 to access an eCOA from the eCOA library 120. The trial server may be initiated within the processing devices 110 of FIG. 1. Initiating the trial session may include associating the participant with a study, wherein the validated instrument is associated with the study. The participant may further be associated with a particular language or locale. The participant may access the trial server via an authorization system (e.g., authorization system 103), with the authorization system including (i) an identity provider web service configured to access a fast healthcare interoperability resource server (e.g., where the eCOAs may be located within the eCOA library 120), and (ii) a firewall.

At step 404, the system (e.g., environment 100 of FIG. 1) may determine, via the trial server (e.g., via the processing devices 110), a validated instrument to be accessed for the trial session. For example, the validated instrument may be an eCOA. The validated instrument may for example be determined by extracting what clinical study a participant is involved in. For example, the validated instrument may be extracted from the studies module 116 or a stored schedule for a clinical study.

At step 406, a request for an instance of the validated instrument may be transmitted to an instrument library (e.g., the eCOA library 120) and via the trial session (e.g., the processing devices 110). The instance of the validated example, may be a reference or pointer to a previously validated instrument. The instance of the validated example may be a validated screenshot of the validated instrument, allowing for the participant to insert answers into the validated screenshot.

At step 408, a data reference object that is operable as a data reference link to the validated instrument stored in the instrument library (e.g., the eCOA library 120) is received from the instrument library, such that the data reference object is operable to execute the validated instrument without generating a copy of the validated instrument.

At step 410 a Graphical User Interface (GUI) of the trial session may operate the data reference object, such that a user device (e.g., computer 700 as described in more detail below) executes the validated instrument by reference. This may allow one or more participants (e.g., user 102) to access the validated instrument through a GUI (e.g., by accessing the server systems 108 through electronic network 106) and to interact and with and respond to the instrument. The results may then be saved to one or more storage devices (e.g., storage devices 112).

Figure 5:
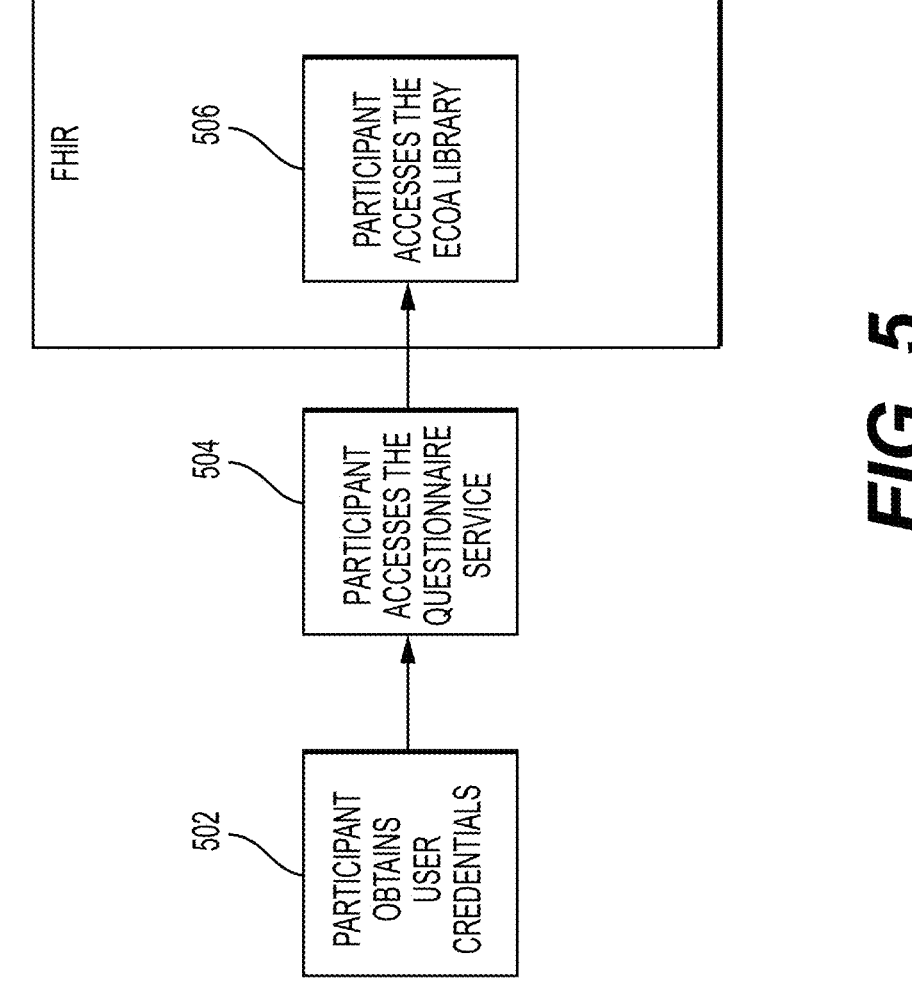
FIG. 5 depicts an exemplary flow diagram illustrating a workflow for obtaining access to a validated instrument, according to one or more embodiments.

FIG. 5 depicts an exemplary flow diagram 500 illustrating a workflow for obtaining access to a validated instrument, according to one or more embodiments. The flow diagram described in FIG. 5 may be performed by the environment 100 of FIG. 1. In other examples, aspects of the flowchart described in FIG. 5 may be performed in external systems and received by the environment 100. Alternatively, the flow diagram described in flowchart 500 may be performed by any computer process system capable of receiving image inputs such as computer 700.

At step 502, a participant may enter user credentials in order to provide initial access to a study. For example, a participant may be introduced to a clinical study. For example, a participant may be selected for a study that a particular organization operates. Upon being selected, a participant may be administered a particular care plan (e.g., a program). The care plan may be participant specific or generated evenly for a study. The participant may, for example, go to organization site to be a participant in the clinical study. The organization site may, for example, have a medical equipment to administer the collection of samples, reading, etc. In another example, the clinical study may be administered in a remote fashion across a large geographical area with a large sample size of participants. A first step may be to provide the participant with credentials to access the study. For example, a participant may be assigned (e.g., associated) with multiple credentials (e.g., a password, code, etc.) where the credential may be associated with a particular participant. The credential may be assigned at an organization cite or online (e.g., through network 106). The credentials may allow a participant to access one or more portions or aspects of the server systems 108 of FIG. 1. For example, the credentials may allow for a participant to access data submitted from a particular organization, data such as questionnaires from the eCOA library 120.

At step 504, the participant may access the questionnaire service (e.g., a particular organization's study). The organization study may for example be administered by an organization sponsor, where the organization sponsor administer the clinical study through a secondary organization. While accessing the organization study, the participant may follow part of a previously developed plan for the clinical trial. The plan may for example have been created and may be administered by the server systems 108.

At step 506, the participant may access the eCOA library (e.g., the eCOA library 120). For example, this access may occur upon completion of a portion of the clinical trial, whereby the research may include a clinical endpoint to meet specific measures set forth to support changes in reported data. For example, a participant (or alternatively, an administer of the clinical study on behalf of the participant) may request authorization of an instrument. For example, a participant (e.g., the user 102) may utilize an authorization system (e.g., the authorization system 103) through a network to request access to the eCOA library. Upon receiving approval, a participant may first complete a contract or fill out identifying information. Next, the participant may obtain access to an eCOA (e.g., through the eCOA library 120). The eCOA may be updated to the participant's locale language my implementing the process described in FIG. 4. The eCOA library may for example be stored in an FHIR server The eCOA may for example be a data reference object that is operable as a data reference link to the validated eCOA in the eCOA library. Through a GUI, the participant may fill out the questionnaire. The answers may then be saved to storage (e.g., storage devices 112) for further analysis (e.g., by the report and analytics module 122).

Figure 6:
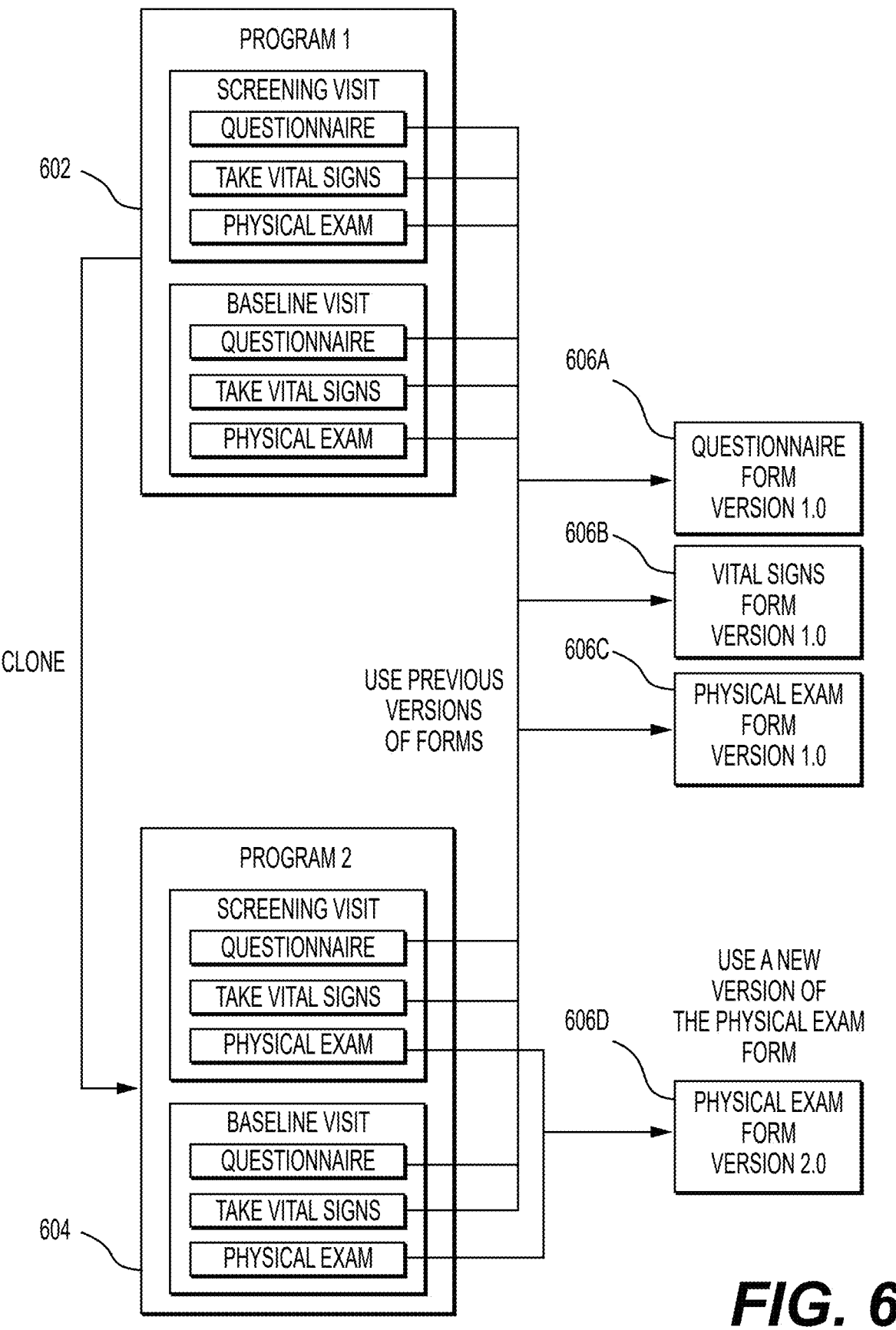
FIG. 6 depicts an exemplary set of programs that are merged to incorporate one or more verified form, according to one or more embodiments.

FIG. 6 depicts an exemplary set of programs that are merged to incorporate one or more verified form, according to one or more embodiments. The programs of FIG. 6 may for example have been created by scheduler 123 of FIG. 1. FIG. 6 may include a first program 602 initially assigned to one or more participants of a clinical trial. FIG. 6 may include a second program 604 that is a new updated program for the particular clinical trial. For the first program 602 and second program 604, two exemplary visits from a phase of the study may be included (e.g., the screening visit and baseline visits), where each visit may include three scheduled events. The methods described herein (e.g., in FIG. 3A) may be applied (e.g., by environment 100 of FIG. 1) to merge the first program 602 and the second program 604.

For example, by using the methods described herein, it may be determined that questionnaire form 606A, vital sign form 606B, and physical exam form 606C may all correspond to forms previously completed and associated with a participant in the clinical trial for the first program 602. These may have been completed prior to the system receiving the second program 604. Upon retrieving the second program 604, the participant's program may be updated to a merged program that includes data objects referencing aspects of the first program and second program. For example, the events that previously occurred (e.g., questionnaire form 606A, vital sign form 606B, and physical exam form 606C), all data objects may be kept, while all remaining data objects of the first program may be deleted. For the second program 604, a current phase and anchor point may be identified utilizing techniques discussed above, and it may be determined that a physical exam form 606D included in the second program 604 has not previously been completed. A new data object referencing the physical exam form 606D may be created for the merged program of the participant.

In an example, the system may be configured to provide a merged program to one or more participants. The merged program may include references to events of the first program and a second program. For example, the merged program may include data objects referencing all past events of the first data object but including no future event (e.g., events that have not occurred for the participant). The merged program may further include data objects referencing all events in the second program that take place after an anchor point of the current phase. The merged program may not require that old study information needs to be transferred to the new program (e.g., as data objects from the first program are maintained). In an example, each participant, on an individual basis, is associated with study data for the events they actually experienced, regardless of changes to scheduling made during the study. This dynamic adjustment for participant-specific study data storage may improve the data storage efficiency of the study, inhibit the creation of filler data that might otherwise be misleading, and streamline data retention and access, as well as other benefits.

It should be understood that, as one or more aspects of the operations discussed above may be performed on a per-participant basis, such operation may result in multiple programs existing within a single study. Such operations also may enable multiple programs within a single study for different groupings of participant, for different sponsors, or any other suitable circumstance or criteria.

Figure 7:
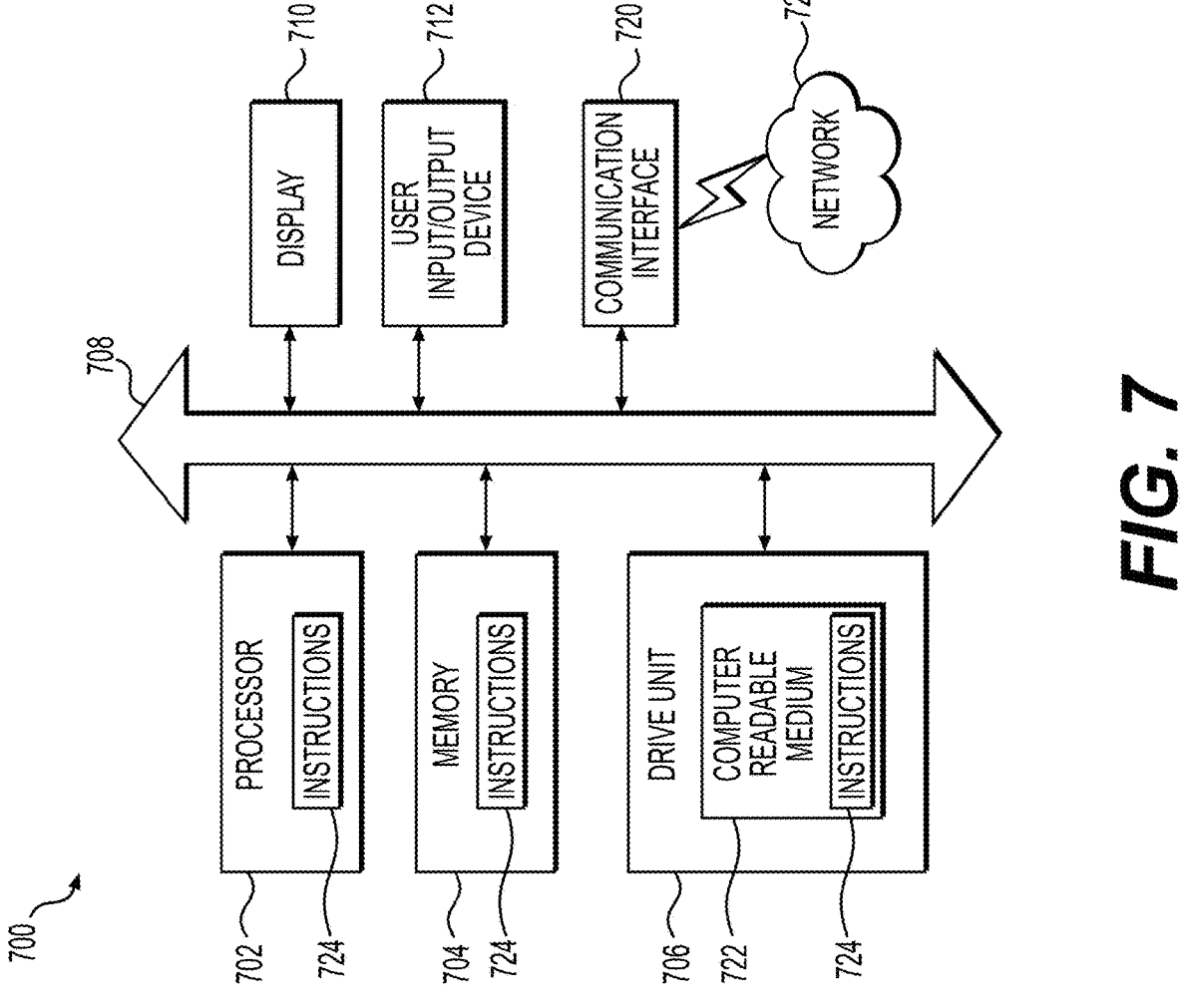
FIG. 7 depicts a simplified functional block diagram of a computer, according to one or more embodiments

FIG. 7 depicts a simplified functional block diagram of a computer, according to one or more embodiments. The computer 700 of FIG. 7 may be utilized by a user 102 or an eCOA manager 104 to access the server systems 108 of FIG. 1. Further the computer 700 may be utilize to execute the methods of FIGS. 3A, 4, and 5, according to exemplary embodiments of the present disclosure. One or more of a processor 702, a memory 704, a drive unit 706, an internal communication bus 708, a display 710, a under input/output ports 712, a communication interface 720, a computer readable medium 722, instructions 724, and a network 725 may communicate by any suitable means. For example, computer 700 may be configured as the server systems 108 and/or another system according to exemplary embodiments of this disclosure. In various embodiments, any of the systems herein may be a computer 700 including, for example, data communication interface 720 for packet data communication. Computer 700 also may include a central processing unit (CPU) 702, in the form of one or more processors, for executing program instructions. Computer 700 may include internal communication bus 708, and storage unit 706 (such as Read-Only Memory (ROM), Hard Disk Drive (HDD), Solid-State Drive (SSD), etc.) that may store data on computer readable medium 722, although computer 700 may receive programming and data via network communications. Computer 700 may also have memory 704 (such as Random-Access Memory (RAM)) storing instructions 724 for executing techniques presented herein, although instructions 724 may be stored temporarily or permanently within other modules of computer 700 (e.g., processor 702 and/or computer readable medium 722). Computer 700 also may include input and output ports 712 and/or display 710 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While the disclosed methods, devices, and systems are described with exemplary reference to transmitting data, it should be appreciated that the disclosed embodiments may be applicable to any environment, such as a desktop or laptop computer, an automobile entertainment system, a home entertainment system, medical equipment, etc. Also, the disclosed embodiments may be applicable to any type of Internet protocol.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments may be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed:

1. A method of utilizing data object references to merge one or more programs, the method comprising:
   initiating, via a server, a session of a study for a user;
   assigning, via the server, a first program of the study to the user, the first program including a plurality of events divided into a plurality of phases,
   generating respective first data objects to reference each event in the first program, wherein the first data objects include first metadata identifying (i) each event in the first program and (ii) the user;
   receiving a second program for the user, the second program including a plurality of second events divided into a plurality of second phases;
   identifying a current phase at which the user will enter the second program;
   generating second data objects to reference each event in the second program that occurs after the current phase, wherein the second data objects include second metadata identifying (i) each event in the second program and (ii) the user; and
   merging the first program and the second program to determine a merged program specific to the user, wherein merging the first program and second program includes:
      identifying and deleting all data objects of the first data object in phases of the first program that have not occurred;
      merging remaining data objects of the first data objects and data objects of the second data objects; and
      storing, at the server, the merged program.

2. The method of claim 1, wherein the first program includes a document, procedure, or data listing that outlines timelines and procedures for the study.

3. The method of claim 1, wherein the current phase corresponds to a beginning phase, a middle phase, an end phase, an event, an event activity, or a recurring activity.

4. The method of claim 1, wherein the first data objects include:
   first data reference links connecting the user to a respective event in the plurality of events in the first program.

5. The method of claim 1, wherein identifying a current phase at which the user will enter the second program includes:
   identifying all phases that have previously occurred in the first program; and
   identifying a next phase to occur in the first program, wherein the next phase is the current phase.

6. The method of claim 1, wherein identifying a current phase at which the user will enter the second program includes:
   identifying all phases that have previously occurred in the first program;
   determining that a user has completed a portion of events in a respective phase of the first program;
   identifying a corresponding phase of the second program;

identifying an anchor point referring to a particular event in the corresponding phase of the second program for the user to begin the second program; and
   generating second data objects for each event in the current phase of the second program that take place after the anchor point.

7. The method of claim 1, further including:
   generating and transmitting, to a user computing device, computer-executable instructions configured to cause the user computing device to display the merged program through a graphical user interface of the user computing device.

8. The method of claim 1, further including:
   identifying a current status for the user, the identifying of the current phase based on the identified current status.

9. A system, the system comprising:
   at least one memory storing instructions; and
   at least one processor configured to execute the instructions to perform operations for determining data integrity, the operations including:
      initiating, via a server, a session of a study for a user;
      assigning, via the server, a first program of the study to the user, the first program including a plurality of events divided into a plurality of phases,
      generating respective first data objects to reference each event in the first program, wherein the first data objects include first metadata identifying (i) each event in the first program and (ii) the user;
      receiving a second program for the user, the second program including a plurality of second events divided into a plurality of second phases;
      identifying a current phase at which the user will enter the second program;
      generating second data objects to reference each event in the second program that occurs after the current phase, wherein the second data objects include second metadata identifying (i) each event in the second program and (ii) the user; and
      merging the first program and the second program to determine a merged program specific to the user, wherein merging the first program and second program includes:
      identifying and deleting all data objects of the first data object in phases of the first program that have not occurred;
      merging remaining data objects of the first data objects and data objects of the second data objects; and
      storing, at the server, the merged program.

10. The system of claim 9, wherein the first program includes a document, procedure, or data listing that outlines timelines and procedures for the study.

11. The system of claim 9, wherein the current phase corresponds to a beginning phase, a middle phase, an end phase, an event, an event activity, or a recurring activity.

12. The system of claim 9, wherein the first data objects include:
   first data reference links connecting the user to a respective event in the plurality of events in the first program.

13. The system of claim 9, wherein identifying a current phase at which the user will enter the second program includes:
   identifying all phases that have previously occurred in the first program; and
   identifying a next phase to occur in the first program, wherein the next phase is the current phase.

14. The system of claim 9, wherein identifying a current phase at which the user will enter the second program includes:

identifying all phases that have previously occurred in the first program;

determining that a user has completed a portion of events in a respective phase of the first program;

identifying a corresponding phase of the second program;

identifying an anchor point referring to a particular event in the corresponding phase of the second program for the user to begin the second program; and generating second data objects for each event in the current phase of the second program that take place after the anchor point.

15. The system of claim 9, further including:

generating and transmitting, to a user computing device, computer-executable instructions configured to cause the user computing device to display the merged program through a graphical user interface of the user computing device.

16. The system of claim 9, further including:

identifying a current status for the user, the identifying of the current phase based on the identified current status.

17. A non-transitory computer readable medium storing processor-readable instructions which, when executed by at least one processor, cause the at least one processor to perform operations including:

initiating, via a server, a session of a study for a user;

assigning, via the server, a first program of the study to the user, the first program including a plurality of events divided into a plurality of phases, generating respective first data objects to reference each event in the first program, wherein the first data objects include first metadata identifying (i) each event in the first program and (ii) the user;

receiving a second program for the user, the second program including a plurality of second events divided into a plurality of second phases;

identifying a current phase at which the user will enter the second program;

generating second data objects to reference each event in the second program that occurs after the current phase, wherein the second data objects include second metadata identifying (i) each event in the second program and (ii) the user; and merging the first program and the second program to determine a merged program specific to the user, wherein merging the first program and second program includes:

identifying and deleting all data objects of the first data object in phases of the first program that have not occurred;

merging remaining data objects of the first data objects and data objects of the second data objects; and storing, at the server, the merged program.

18. The non-transitory computer readable medium of claim 17, wherein the first program includes a document, procedure, or data listing that outlines timelines and procedures for the study.

19. The non-transitory computer readable medium of claim 17, wherein the current phase corresponds to a beginning phase, a middle phase, an end phase, an event, an event activity, or a recurring activity.

20. The non-transitory computer readable medium of claim 17, wherein the first data objects include:

first data reference links connecting the user to a respective event in the plurality of events in the first program.

* * * * *